US00PP24022P3

(12) United States Plant Patent
Zwetzig

(10) Patent No.: US PP24,022 P3
(45) Date of Patent: Nov. 12, 2013

(54) ***HIBISCUS* PLANT NAMED 'SMALL WONDERS'**

(50) Latin Name: *Hibiscus moscheutos×H. coccineus*
Varietal Denomination: Small Wonders

(75) Inventor: Gretchen Zwetzig, Lindsay, CA (US)

(73) Assignee: Gretchen Zwetzig-Fleming's Flower Fields, Inc., Lindsay, CA (US)

( * ) Notice: Subject to any disclaimer, the term of this patent is extended or adjusted under 35 U.S.C. 154(b) by 115 days.

(21) Appl. No.: 12/932,358

(22) Filed: Feb. 24, 2011

(65) Prior Publication Data

US 2012/0222177 P1 Aug. 30, 2012

(51) Int. Cl.
*A01H 5/00* (2006.01)

(52) U.S. Cl.
USPC ..... Plt./257

(58) Field of Classification Search
USPC ..... Plt./257
See application file for complete search history.

(56) References Cited

PUBLICATIONS

The New Orleans, Louisana Chapter of the American *Hibiscus* Society May 25, 2008, pp. 1-11.*
Small Wonders, retrieved on Jul. 22, 2013. 2 pp.*

* cited by examiner

*Primary Examiner* — June Hwu

(57) ABSTRACT

A new and distinct cultivar of winter hardy *Hibiscus* plant named 'Small Wonders' is the result of a unique hybridization. This new and distinct cultivar is characterized primarily as to its novelty by its extreme cold hardiness to Zone 4, medium thick-textured, heavily streaked and speckled, red, white and pink flowers and its "Maple-shaped" foliage with a black-purple coloration, compactness of approximately 2½ feet, its vigorous and uniform breaking habit and its floriferous nature from midsummer until frost.

2 Drawing Sheets

Latin name: *Hibiscus moscheutos×H. coccineus.*

Varietal denomination: 'Small Wonders'.

FIELD OF THE INVENTION

This plant, as a hybridized hardy *Hibiscus*, is valuable to the landscape market for its improvements in thicker textured and vividly colored flowers and buds, refined "maple-like" foliage with a dark purple color, its all-around vigor, good compact breaking action, and adaptation to extreme environments, including the ability to consistently survive winter temperatures of at least −30 degrees Fahrenheit.

BACKGROUND OF THE NEW PLANT

The new plant of this invention is the result of a unique hybridization, with the breeding achievement being evidenced in the outstanding combination of characteristics exhibited by this new and distinct *Hibiscus* plant, which include:

(a) Refined, 3-5 lobed "maple-shaped" leaves of a black-purple color and relatively smooth margins which combined compliments the landscape;
(b) Medium-sized flowers that are outstanding for their red, white and pink colored, heavily streaked and speckled petals (on both sides);
(c) The plant being very floriferous with flowers that stay open for at least one to two days;
(d) The plant being small to medium-sized but vigorous with compact and uniform breaking action which gives it unique landscape utility; and (e) The plant being so hardy that it can consistently withstand winter temperatures of at least −30 degrees Fahrenheit.

SUMMARY OF THE INVENTION

'Small Wonders' was the result of a 50-year breeding program. Its ancestry includes *Hibiscus moscheutos* and *Hibiscus coccineus*. More specifically, the plant resulted from multiple crossings with an unnamed, Fleming-bred *Hibiscus moscheutos* (non patented) and an unnamed Fleming-bred *Hibiscus coccineus* (non patented). The seedling which most nearly met all of the above standards was selected.

This new plant first bloomed in the summer of 2001 and was selected by Gretchen Zwetzig on her property located at 8101 S. 14th St. 68512 Lincoln, Nebr. (previous address for applicants). Asexual propagation of the plant by cuttings and root division in Lincoln, Nebr. has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy *Hibiscus* plant greatly contributes to the market with its, stunning beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar at 2½ years of age are shown in the attached photographs.

More specifically.

Figure 1:
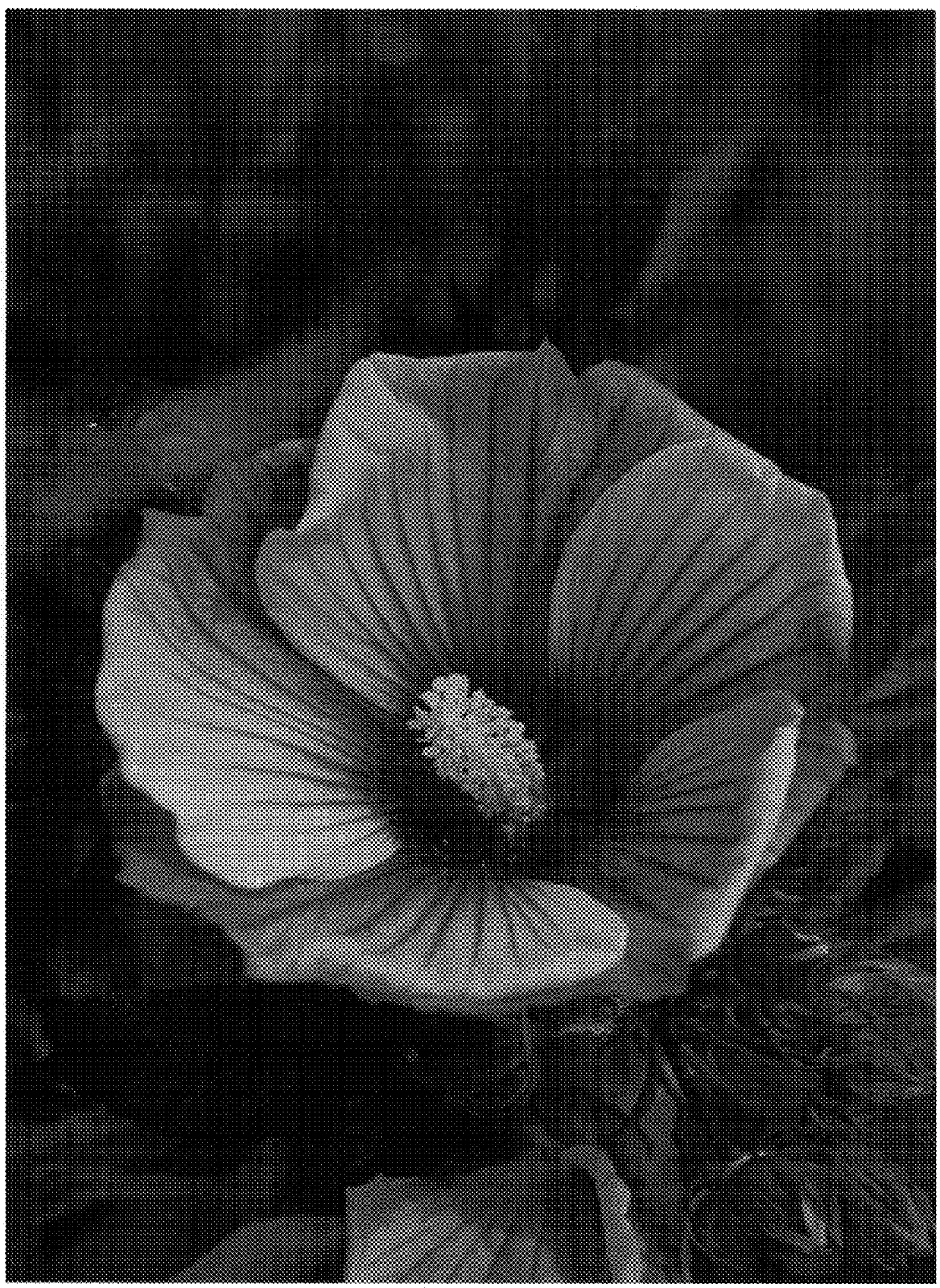
FIG. 1 is a close-up of the flower and the flower buds.
Figure 2:
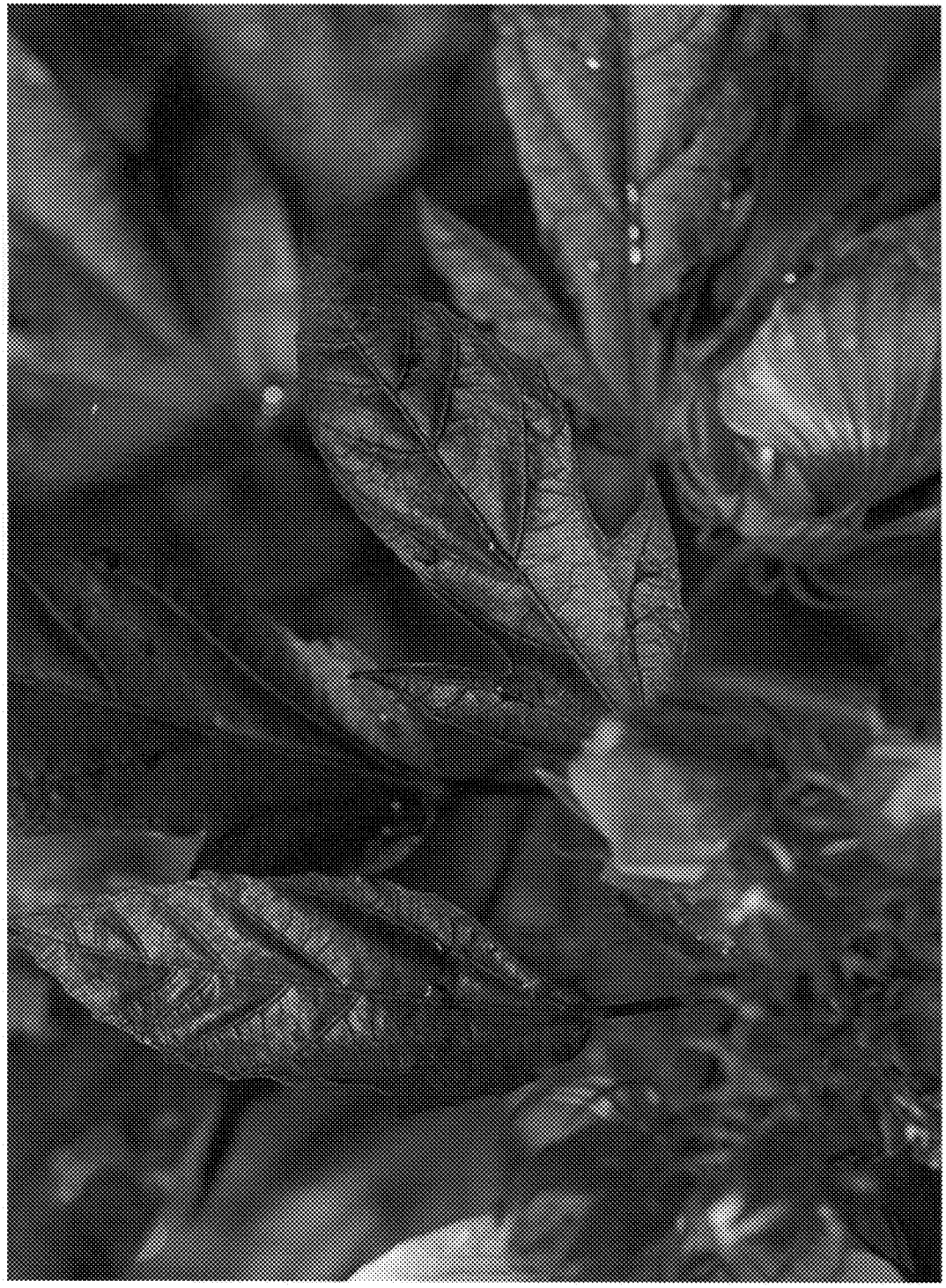
FIG. 2 is a close-up of the leaf and bud.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The Royal Horticultural Society Colour Chart (2001), while general color recitations are consistent with ordinary American terminology.

'Small Wonders' has not been observed under all possible environmental conditions. It is to be understood that the phenotype may vary significantly with variations in the environment such as temperature, light intensity, humidity, and day length without, however any difference in genotype of the plant. The following botanical characteristics and observations are gathered from the plant when grown in Lincoln, Nebr. (USDA Zone 4) and Lindsay, Calif. (USDA Zone 9).

THE PLANT

Parentage:

*Seed parent.*—*Hibiscus moscheutos*, unnamed and unpatented Flemings-bred seedling.

*Pollen parent.*—*Hibiscus coccineus*, unnamed and unpatented Fleming-bred seedling.

Comparison between observed plant and parents: Parents were similar, except for being approximately ½ foot taller in height than Observed Plant.

Comparison between observed plant and other known cultivars: The Observed Plant is unique, but most similar to patents: 'Crown Jewels' U.S. Plant Pat. No. 11,857 among the other patented hardy *Hibiscus* from Flemings, in that:

(a) they are all more compact at 3 feet on average.

(b) they are all hardy to −30 degrees Fahrenheit.

(c) they all have refined new leaf shapes and colors. But, 'Small Wonders' has darker purple leaves.

(d) they all have thick, overlapping new flower colors with blooms from the top to the bottom of the plant. 'Small Wonders' has more streaking from flower center.

Origin: A selected seedling from stated cross.

Type of plant: Hardy, herbaceous perennial.

Classification: Variety of hardy *Hibiscus* plant.

Propagation: Relatively easy to propagate through cuttings; holds its distinguishing characteristics through successive cuttings and divisions.

Size: About 2½ to 3 feet tall and about 2½ feet wide.

Form: Symmetrical annual growth from perennial roots.

Habit: Upright and uniformly branched.

Growth: Vigorous; medium and compact. Full grown (2½ to 3 ft) in 2 years. 2 ft 8 inches or 32 inches when measured.

Hardiness: Hardy to at least −30 degrees Fahrenheit.

General health: Plant is very disease resistant against rot, aphids, spider mites, scale, white fly etc.; sturdy through excessive drought, rain or wind.

Propagation: Relatively easy and fast rooting in approximately 2 weeks.

Foliage:

1. *Arrangement.*—Alternate.
2. *Shape.*—Juvenile: Ovate to 3-5 lobed "maple-shaped" leaves. Rounded base shape. Mature: Refined, "maple-shaped", 3-5 lobed leaf with entire to mildly serrate margins and acute apices; rounded base.
3. *Size.*—Mature leaf (petiole base to apex): Length is about 6 inches or (15 cm), width is about 3 inches or (7.5 cm). Young leaf: Length 2½ inches or (6.5 cm), width is 1½ inches or (4 cm).
4. *Color.*—Young leaves: N 77-A. Mature leaves: (upper side): Between N 77-A and N 79-A. Veins: Venation pattern: Palmate. Upper Venation Color: N 79-A Mature Leaf. Coloration of the lower leaf surface: Mature: Between 148-B and 149-B. Young: closest to 147-B.
5. *Surface texture.*—Upper: Smooth. Lower: Semi-smooth.
6. *Petiole length.*—About 2¾ inches or 6.985 cm. Diameter: 1-2 cm.
7. *Petiole color.*—137-A and N 77-A. Surface texture: Semi smooth.

Stems: The stems are stout at the base becoming more slender toward the apices; coloration is consistent with the petiole.

Length: 2-3 inches.

Diameter: 1-2 cm.

Internode length: Apx. 2 inches.

Texture: Semi-smooth.

The Flower

Blooming period: Profuse from July until frost.

Flower diameter: Medium to large; about 8-10 inches (20.32-25.4 cm).

Borne: Singly in leaf axils, from midpoint of stems upward.

Bloom duration: Individual bloom lasts at least one to two full days.

Form: Campanulate; petals are also very overlapping.

Average number of flowers per season: 300.

Bud:

1. *Length.*—About 2¼ inches or (5.715 cm) on day before opening. Diameter: apx. 2 inches.
2. *Color.*—61-B, C, and D.
3. *Surface texture.*—Semi-glabrous.
4. *Duration.*—One to two weeks.

Corolla: Having five petals.

1. *Petal character and dimensions.*—Campanulate and very overlapping. (a) Length: About 4-5 inches or (10.16-12.7 cm). (b) Width: About 4-5 inches or (10.16-12.7 cm).
2. *Coloration.*—Red, white and pink. 69-D, 59-A, 60-A and 53-A. (a) Margins: (Front and back): 67-B. Background coloration of petal surface: Whiter than 69-D. Both front and back. (b) Venation color in petals: 67-B and 53-A (same on petal backside). (c) Eye zone: Between 59-A and 60-A. Size: 3 inches or (7.5 cm).
3. *Texture.*—Smooth.
4. *Substance.*—Thick.
5. *Shape.*—Campanulate and very overlapping with petal folds at edges.

Reproductive organs:

1. *Staminal column.*—Stamen along basal two-thirds. Stamen length: About 1¾ inches or (4.445 cm). (on average). Filament (anthers) length: 1¼"; 3.175 cm. Stamen Color Designation: Lighter than 11-D with N 74 A (streaks). Pollen color: 162-B. Average no. stamens: 5.

2. *Style.*—Terminates upper one-third of stamina column. Stigmatic lobe color (style color): 11-D (tips: 63-A). Stigma average size: ½", 1.27 cm.

Calyx: Connate at the base; about 1¼ inches or (3.175 cm) in length. Color: Medium green: 147-A. Inside and Outside. Calyx average number: 1; Shape: 5-lobed, connate at base. Surface texture: Semi-smooth.

Stipules: None.

Seed (fruit): Size: 1 cm. Color: Grey-brown. Average number: Less than 100.

Epicalyx: Whorl of bracts.

1. *Shape.*—10-12 slender, sword-shaped bractlets.
2. *Length.*—About 1½ inches or (3.8 cm).
3. *Color.*—144-A. Upper and Lower Surface.

Peduncle:

1. *Length.*—About 2 inches or (5.08 cm). Diameter: 1 cm.
2. *Strength.*—Stiff and sturdy.
3. *Color.*—Light to medium green with slight reddish-purple cast. 148-A and 175 A.
4. *Surface texture.*—Semi-smooth.

The invention claimed is:

1. A new and distinct cultivar of hardy *Hibiscus* plant, as herein shown and described, characterized by its compact nature, refined "maple-shaped" foliage of an extremely dark purple coloration, its large heavily streaked and speckled, red, white and pink flowers, its vigor and its hardiness.

* * * * *